US010456164B2

(12) United States Patent
Snoke et al.

(10) Patent No.: US 10,456,164 B2
(45) Date of Patent: Oct. 29, 2019

(54) ANTI-MICROBIAL MEDICAL INJECTION ASSEMBLIES FOR ONABOTULINUMTOXINA DELIVERY AND METHODS OF USE THEREOF

(71) Applicant: URO-1, Inc., Winston-Salem, NC (US)

(72) Inventors: Phillip Jack Snoke, Winston-Salem, NC (US); Philip Morrison Allred, III, Kernersville, NC (US); John Joseph Smith, Winston-Salem, NC (US)

(73) Assignee: URO-1, INC., Winston-Salem, NC (US)

( * ) Notice: Subject to any disclaimer, the term of this patent is extended or adjusted under 35 U.S.C. 154(b) by 0 days.

(21) Appl. No.: 15/722,168

(22) Filed: Oct. 2, 2017

(65) Prior Publication Data

US 2019/0099198 A1 Apr. 4, 2019

(51) Int. Cl.
| | | |
|---|---|---|
| A61M 5/315 | (2006.01) | |
| A61B 17/34 | (2006.01) | |
| A61K 9/00 | (2006.01) | |
| A61B 17/20 | (2006.01) | |
| A61M 5/178 | (2006.01) | |
| A61K 38/48 | (2006.01) | |
| A61M 37/00 | (2006.01) | |

(52) U.S. Cl.
CPC .......... *A61B 17/3417* (2013.01); *A61B 17/20* (2013.01); *A61K 9/0019* (2013.01); *A61K 38/4893* (2013.01); *A61M 5/178* (2013.01); *A61M 37/00* (2013.01)

(58) Field of Classification Search
CPC ............ A61B 1/00066; A61B 1/00174; A61B 1/00179; A61B 1/00183
USPC .................. 600/121–125, 127, 129, 153, 156
See application file for complete search history.

(56) References Cited

U.S. PATENT DOCUMENTS

| 5,386,817 A * | 2/1995 | Jones ................. A61B 1/00091 138/108 |
| 5,435,805 A * | 7/1995 | Edwards ............ A61B 10/0233 604/22 |
| 5,483,951 A | 1/1996 | Frassica et al. |
| 5,486,161 A | 1/1996 | Lax |
| 5,526,822 A | 6/1996 | Burbank et al. |
| 5,607,435 A * | 3/1997 | Sachdeva ............. A61B 1/0058 359/819 |
| 5,849,011 A * | 12/1998 | Jones ................. A61B 18/1477 606/47 |
| 5,873,877 A * | 2/1999 | McGaffigan ....... A61B 1/00096 606/41 |

(Continued)

*Primary Examiner* — Matthew J Kasztejna
(74) *Attorney, Agent, or Firm* — Cooper & Dunham LLP

(57) ABSTRACT

A medical injection assembly is provided and includes an introducer with a handle, a sheath, a scope lumen configured to receive an endoscope at a first proximal end of the handle and hold the endoscope in a desired position, a cap attached to the distal end of the scope lumen configured to isolate the scope lumen from the external environment, and a cannula lumen configured to receive a cannula at a second proximal end of the handle and hold the cannula in a desired position. The medical injection assembly includes a cannula configured such that the distance between the distal tip of the cannula and the axis defined by the sheath of the introducer increases as the cannula is moved in a distal direction and a syringe.

14 Claims, 8 Drawing Sheets

Exhibit A

(56) References Cited

U.S. PATENT DOCUMENTS

| | | | |
|---|---|---|---|
| 5,993,447 A * | 11/1999 | Blewett | A61B 18/1477 600/105 |
| 6,059,734 A | 5/2000 | Yoon | |
| 6,106,521 A * | 8/2000 | Blewett | A61B 18/1477 600/105 |
| 6,126,633 A | 10/2000 | Kaji | |
| 6,296,633 B1 | 10/2001 | Helgerson | |
| 6,350,231 B1 | 2/2002 | Ailinger et al. | |
| 6,358,197 B1 * | 3/2002 | Silverman | A61F 2/04 600/29 |
| 6,428,538 B1 * | 8/2002 | Blewett | A61B 18/1485 606/41 |
| 6,530,881 B1 | 3/2003 | Ailinger et al. | |
| 6,733,440 B2 | 5/2004 | Ailinger et al. | |
| 6,855,124 B1 * | 2/2005 | Gonzalez | A61B 17/3478 604/164.1 |
| 6,869,394 B2 * | 3/2005 | Ishibiki | A61B 1/00089 600/121 |
| 7,309,317 B2 | 12/2007 | Miller et al. | |
| 8,088,081 B2 | 1/2012 | Field et al. | |
| 8,277,373 B2 * | 10/2012 | Maahs | A61B 1/0008 600/104 |
| 8,394,068 B2 | 3/2013 | Kosinski | |
| 8,939,897 B2 * | 1/2015 | Nobis | A61B 1/2736 600/127 |
| 9,642,712 B2 | 5/2017 | Schaller | |
| 2001/0007076 A1 | 7/2001 | Jesseph | |
| 2003/0073902 A1 * | 4/2003 | Hauschild | A61B 17/32037 600/431 |
| 2004/0013652 A1 * | 1/2004 | Marko | A61K 31/715 424/93.7 |
| 2008/0058595 A1 * | 3/2008 | Snoke | A61B 1/00135 600/114 |
| 2008/0177225 A1 | 7/2008 | Matsumoto | |
| 2009/0143698 A1 | 6/2009 | Janssens | |
| 2012/0143006 A1 * | 6/2012 | Avitsian | A61B 1/00066 600/121 |
| 2012/0259203 A1 | 10/2012 | Devereux | |
| 2014/0200402 A1 * | 7/2014 | Snoke | A61B 17/42 600/104 |
| 2014/0213932 A1 | 7/2014 | Knoll et al. | |
| 2016/0166331 A1 | 6/2016 | Leimbach et al. | |
| 2016/0166772 A1 | 6/2016 | Mirzazadeh | |

\* cited by examiner

Exhibit A

ANTI-MICROBIAL MEDICAL INJECTION ASSEMBLIES FOR ONABOTULINUMTOXINA DELIVERY AND METHODS OF USE THEREOF

BACKGROUND

Approximately 16.0% of the United States population suffers from Overactive Bladder (OAB). Because OAB is a chronic condition, treatments must be administered on a periodic basis to control the systems. Injections of OnabotulinumtoxinA, marketed under the trade name Botox, have proven effective in treating OAB for longer periods of time with low incidence of adverse events. Current methods of delivering OnabotulinumtoxinA to the bladder involve inserting a cystoscope and needle through the urethra to the bladder and manipulating the entire assembly both laterally and along the axis of the urethra as a unit to inject the medication into the bladder wall. Because the cystoscope and needle are moved together during this procedure, current devices and their methods of use result in significant patient discomfort and possible damage to the urethra.

The placement and pattern of the multiple injections in the bladder are associated with significantly improved treatment outcomes. Thus, it is important that devices and methods of injecting OnabotulinumtoxinA into the bladder offer physicians performing the procedure precise control. However, it is difficult to create precise injection patterns using current devices and methods because the scope moves with the needle when aiming for a new injection site. Moreover, said devices are usually not disposable, and must be disassembled and sterilized after each use, making them difficult to maintain and increasing the risk of contamination or infection.

Endoscopes, more particularly, cystoscopes, are commonly used in injection procedures to visualize the target injection sites on the bladder. In prior art systems, endoscopes are exposed to the bodily fluids of the patient, requiring them to be sterilized after each injection procedure. Proper sterilization of endoscopes requires a process that may take up 48 hours, during which time the endoscope may not be used. Physicians must thus schedule fewer procedures or purchase more endoscopes.

What is needed, therefore, is a device that can inject OnabotulinumtoxinA in precise patterns on the bladder wall while minimizing lateral movement of the device itself while in the urethra to decrease patient discomfort and probability of urethral injury. Furthermore, said device should be simple enough to keep manufacturing costs at a minimum so that the device may be disposable. The device must also isolate endoscopes used in conjunction with the device from the external environment and bodily fluids of the patient without impairing the visual fidelity of the endoscope.

SUMMARY OF THE INVENTION

The present invention relates to a medical injection assembly directed towards the treatment of Overactive Bladder by injecting OnabotulinumtoxinA into bladder tissue while maintaining the sterility of endoscopes used in the procedure. The present invention is also directed towards a flexible cannula with high tensile strength and buckling resistance for use in said medical injection assemblies.

In one embodiment of the present invention, a medical injection assembly may include an introducer. The introducer may include a handle, a sheath, and a scope lumen configured to receive an endoscope at a first proximal end of the handle and hold the endoscope in a desired position. The introducer may further include an optically-clear, fluid-tight cap attached to the distal end of the scope lumen configured to isolate the scope lumen from the external environment. The introducer may further include a cannula lumen configured to receive a cannula at a second proximal end of the handle and hold the cannula in a desired position. The introducer may further include at least one fluid lumen configured to channel fluid to and from the distal end of the sheath. The medical injection assembly may further include a cannula configured such that the distance between the distal tip of the cannula and the axis defined by the sheath of the introducer increases as the cannula is moved in a distal direction. The medical injection assembly may further include a syringe connected to the proximal end of the cannula.

In one embodiment of the present invention, the optically-clear, fluid-tight cap is comprised of silicon.

In one embodiment of the present invention, the optically-clear, fluid-tight cap is configured to deform to the shape of the endoscope without distorting the optical properties of the seal.

In one embodiment of the present invention, the plane defined by the optically-clear, fluid-tight cap intersects the axis defined by the sheath at an angle of about 60 degrees.

In one embodiment of the present invention, the cannula may include a needle attached to a distal tip of the cannula. The cannula may further include a first fluid connector attached to a proximal end of the cannula. The cannula may be comprised of a biocompatible thermoplastic polymer and a distal portion of the cannula may maintain a predefined curvature in the absence of a deforming force.

In one embodiment of the present invention, wherein the diameter of the needle is less than the diameter of the cannula.

In one embodiment of the present invention, the needle may be a 23 gauge needle.

In one embodiment of the present invention, the biocompatible thermoplastic polymer may have a flexural modulus of about 595,000 psi.

In one embodiment of the present invention, the biocompatible thermoplastic polymer may be polyether ether-ketone (PEEK).

In one embodiment of the present invention, the predefined curvature may be defined by an inverse tangent function.

In one embodiment of the present invention, the medical injection assembly may further include an endoscope.

In one embodiment of the present invention, the endoscope may be a cysto scope.

In one embodiment of the present invention, a method for treating overactive bladder may include inserting an endoscope into a scope lumen of an introducer, wherein an optically-clear, fluid-tight cap attached to the distal end of the scope lumen is configured to isolate the endoscope from the external environment. The method may further include inserting a cannula into a cannula lumen of the introducer, the cannula configured such that the distance between the distal tip of the cannula and the axis defined by the sheath of the introducer increases as the cannula is moved in a distal direction, wherein a syringe filled with OnabotulinumtoxinA is coupled to the proximal end of the cannula. The method may further include guiding the introducer through the urethra of a patient to the patient's bladder. The method may further include extending the distal portion of the cannula past the distal end of the introducer until a needle attached to the distal end of the cannula is placed at a desired radial distance from the axis defined by the sheath of the introducer. The method may further include rotating the introducer to position the needle at a desired position. The method may further include moving the introducer in a distal direction to insert the needle into the bladder. The method may further include activating the syringe to inject OnabotulinumtoxinA into the bladder. The method may further include moving the introducer in a proximal direction to remove the needle from the bladder. The method may further include repeating the extending, rotating, moving distally, activating, and moving proximally steps until a therapeutically effective amount of OnabotulinumtoxinA has been injected in a therapeutically effective pattern into the bladder.

Still other aspects, features, and advantages of the invention are readily apparent from the following detailed description when illustrated by a number of particular embodiments and implementations, including the best mode contemplated for carrying out the invention. The invention is also capable of other and different embodiments, and several details can be modified in various obvious respects, all without departing from the spirit and scope of the invention. Accordingly, the drawings and description are to be regarded as illustrative in nature, and not as restrictive.

DETAILED DESCRIPTION

Figure 1:
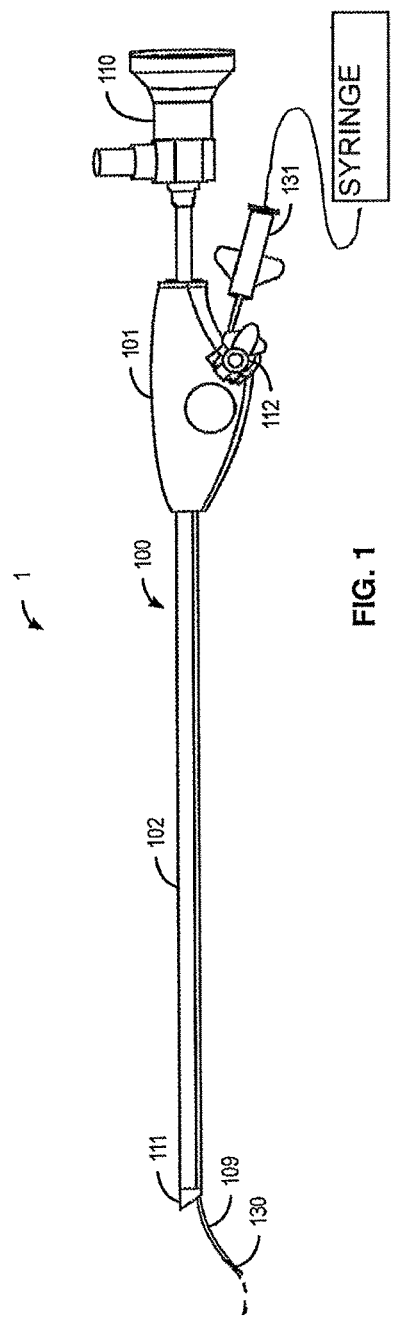
FIG. 1 is a side view of a medical injection assembly according to one embodiment of the present invention.
Figure 2:
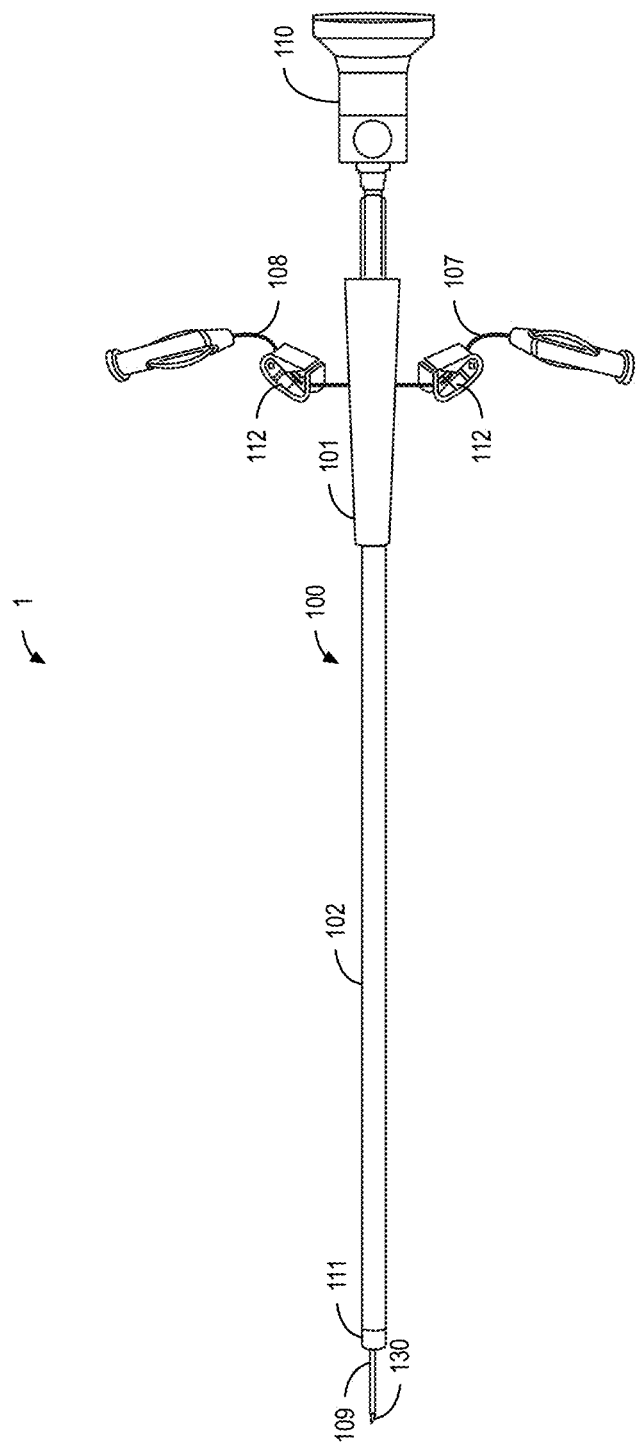
FIG. 2 is a top-down view of a medical injection assembly according to one embodiment of the present invention.
Figure 3:
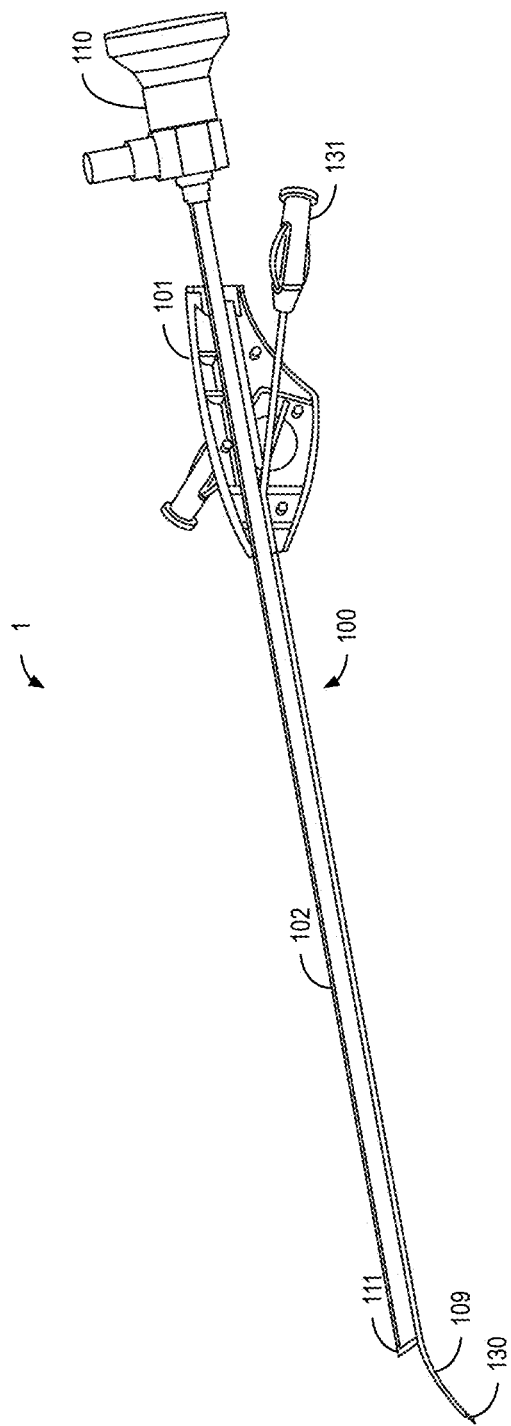
FIG. 3 is a cut-away isometric view of a medical injection assembly according to one embodiment of the present invention.
Figure 4:
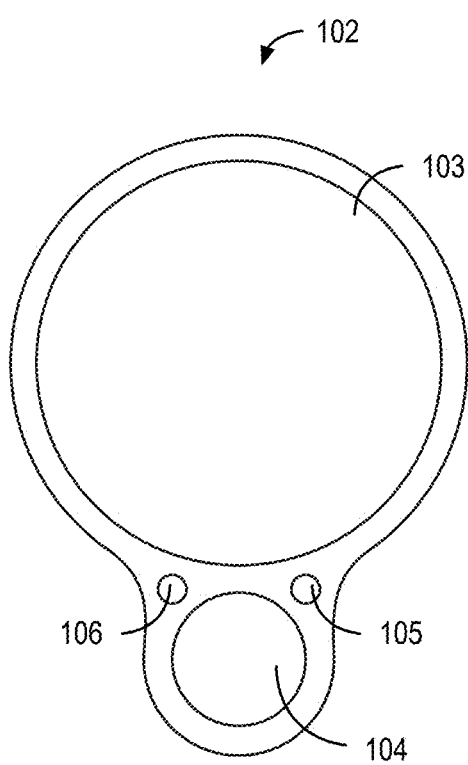
FIG. 4 is a cross-section of a sheath of an introducer according to one embodiment of the present invention.
Figure 5:
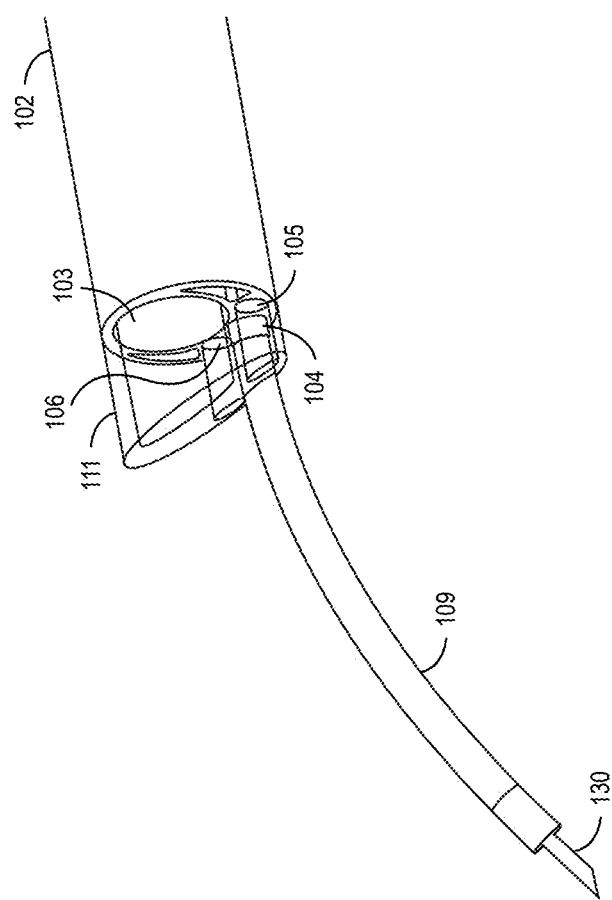
FIG. 5 is a side view of the distal tip of an introducer according to one embodiment of the present invention.
Figure 6:
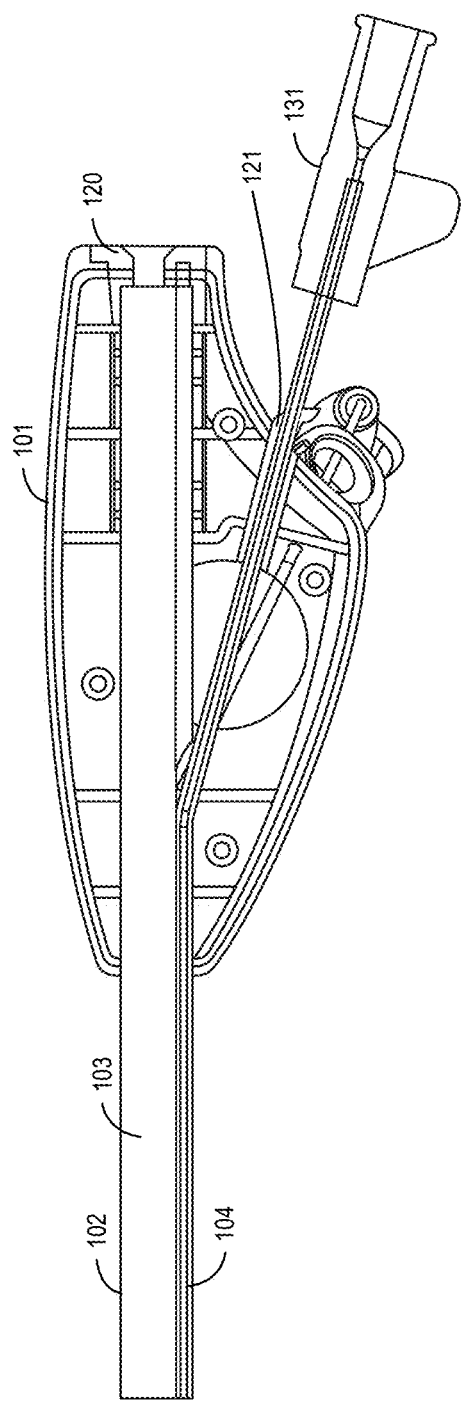
FIG. 6 is a cut away view of the handle of an introducer according to one embodiment of the present invention.

In the following description, for the purposes of explanation, numerous specific details are set forth in order to provide a thorough understanding of the embodiments of the invention. One skilled in the art will recognize that the embodiments of the invention may be practiced without these specific details or with an equivalent arrangement. In other instances, well-known structures and devices are shown in block diagram form in order to avoid unnecessarily obscuring the embodiments of the invention.

The presently disclosed subject matter is presented with sufficient details to provide an understanding of one or more particular embodiments of broader inventive subject matters. The descriptions expound upon and exemplify particular features of those particular embodiments without limiting the inventive subject matters to the explicitly described embodiments and features. Considerations in view of these descriptions will likely give rise to additional and similar embodiments and features without departing from the scope of the presently disclosed subject matter.

Referring now to FIGS. 1 through 6, a medical injection assembly 1 according to an embodiment of the present invention is shown. The medical injection assembly 1 may comprise an introducer 100. The introducer 100 may comprise a handle 101, and sheath 102, a scope lumen 103 configured to receive an endoscope 110 at a first proximal end of the handle 101 and hold the endoscope 110 in a desired position, an optically-clear, fluid-tight cap 111 attached to the distal end of the scope lumen 103 configured to isolate the scope lumen 103 from the external environment, and a cannula lumen 104 configured to receive a cannula 109 at a second proximal end of the handle 101 and hold the cannula 109 in a desired position. The medical injection assembly 1 may further comprise a cannula 109 configured such that the distance between the distal tip of the cannula 109 and the axis defined by the sheath 102 of the introducer 100 increases as the cannula 109 is moved in a distal direction. The medical injection assembly 1 may further comprise a syringe connected to the proximal end of the cannula.

The sheath 102 of an introducer 100 according to an embodiment of the present invention may include a scope lumen 103, cannula lumen 104, and at least one fluid lumen. In preferred embodiments, the sheath may include two fluid lumens 105, 106. A first fluid line 107 and fluid source may be connected to the proximal end of the first fluid lumen 105 to channel fluid to the distal end of the sheath 102. A second fluid line 108 and a vacuum source may be connected to the proximal end of the second fluid lumen 106 to channel fluid away from the distal end of the sheath 102. The fluid lines 107, 108 may further comprise pinch valves or roller valves 112 to control the flow of the fluid.

Scope lumen 103 may be configured to receive a variety of endoscopes 110 for illuminating and visualizing target tissue within the body. In preferred embodiments, the endoscope 110 may be a cystoscope. The diameter of the scope lumen 103 should be sufficient to fit industry standard cystoscopes known in the art. In preferable embodiments, the scope lumen 103 may have a diameter of about 4 mm to about 5 mm.

The optically-clear, fluid-tight cap 111 attached to the distal end of the scope lumen 103 may be configured to isolate the scope lumen 103 from the external environment. In preferred embodiments, the cap 111 may be comprised of silicon or other similar materials that are not water permeable and allow light to pass through with minimal distortion. The circumference of the cap 111 may be welded or glued to the distal end of the sheath 102 or to the distal opening of the scope lumen 103. One of ordinary skill in the art will appreciate that the cap 111 may be attached to the distal end of the sheath 102 or the distal opening of the scope lumen 103 by any means of adjoining two poymers known in the prior art. In preferred embodiments, the cap 111 may be overmolded directly onto the distal end of the sheath 102 or the distal opening of the scope lumen 103.

In some embodiments, the cap 111 may also be configured to deform to the shape of the endoscope 110 without distorting the optical properties of the cap 111. In yet other embodiments, the plane defined by the distal end of the optically-clear fluid tight cap 111 may intersect the axis defined by the sheath 102 at an angle of about 60 degrees.

The cannula lumen 104 may be configured to receive a cannula 109 according to the present invention as further described herein. The diameter of the cannula lumen 104 should be sufficient to fit said cannulas 109. In preferred embodiments, the cannula lumen 104 may have a diameter of about 1 mm to about 2 mm. The walls of the sheath 102 must be minimized so as to allow the introducer to fit through a patient's urethra while maintaining its strength and rigidity. In preferred embodiments, the sheath 102 walls may have a thickness of about 0.1 mm to about 0.4 mm. The sheath 102 may be comprised of polyether block amides, polyethylene, or other materials with similar rigidity characteristics.

The scope lumen 103 may extend from a proximal end of the handle 101 and may be configured to receive an endoscope 110 from a proximal end of the handle 101. A scope seal 120 may be positioned at a proximal end of the handle 101 to engage an endoscope 110. The scope seal 120 may be comprised of a material with coefficient of friction sufficient to hold an endoscope 110 in place. In preferable embodiments, the scope seal 120 may be comprised of silicone.

The cannula lumen 104 may extend from a proximal end of the handle 101 and may be configured to receive a cannula 109 from a proximal end of the handle 101. A cannula seal 121 may be positioned at a proximal end of the handle 101 to engage a cannula 109. The cannula seal 121 may be comprised of a material with coefficient of friction sufficient to hold a cannula 109 in place. In preferable embodiments, the cannula seal 121 may be comprised of silicone.

According to some embodiments, the cannula 109 may comprise a needle 130 attached to a distal tip of the cannula 109. The cannula may further comprise a first fluid connector 131 attached to a proximal end of the cannula 109, wherein the cannula 109 may be comprised of a biocompatible thermoplastic polymer, and wherein a distal portion of the cannula 109 may maintain a predefined curvature in the absence of a deforming force.

The needle 130 may be any commercially available hypodermic needle suitable for performing injections of OnabotulinumtoxinA. In preferred embodiments, the diameter of the needle 130 is less than the diameter of the cannula 109, and the needle 130 may be a 23 gauge needle and may extend past the cannula 109 about 1.0 mm to about 3.0 mm in length. In such configurations, the distal tip of the cannula 109 acts as a wall, preventing the needle 130 from penetrating into the target tissue past the distal tip of the cannula 109.

The biocompatible thermoplastic polymer may be any such polymer having a flexural modulus of about 595,000 psi. Importantly, such a flexural modulus allows the user of the device to insert the needle 130 into bladder tissue without causing the cannula 109 itself to bend or deform in a clinically significant manner. In preferred embodiments, the biocompatible thermoplastic polymer may be polyether ether-ketone (PEEK).

The cannula 109 may be configured such that the distance between the distal tip of the cannula 109 and the axis defined by the sheath 102 of the introducer 100 increases as the cannula is moved in a distal direction. According to at least one embodiment of the present invention, such a configuration may be achieved by forming the cannula such that a distal portion of the cannula maintains a predefined curvature in the absence of a deforming force. Thus, as the distal portion of the cannula exits the distal end of the introducer, it returns to a predefined curvature that causes the distal tip of the cannula to move away from the axis defined by the sheath of the introducer. In preferred embodiments, the predefined curvature may be defined by an inverse tangent function. But one of ordinary skill in the art will recognize that any predefined curvature that causes the distal tip of the cannula to move away from the axis defined by the sheath 102 of the introducer 100 may be used in the present invention.

According to another embodiment of the present invention, a method for treating overactive bladder may comprise inserting an endoscope 110 into a scope lumen 103 of an introducer 100, wherein an optically-clear, fluid-tight cap 111 attached to the distal end of the scope lumen 103 is configured to isolate the endoscope 110 from the external environment. The method may further comprise inserting a cannula 109 into a cannula lumen 104 of the introducer 100, the cannula 109 configured such that the distance between the distal tip of the cannula 109 and the axis defined by the sheath 102 of the introducer 100 increases as the cannula 109 is moved in a distal direction, wherein a syringe filled with OnabotulinumtoxinA is coupled to the proximal end of the cannula 109. The method may further comprise guiding the introducer 100 through the urethra of a patient to the patient's bladder. The method may further include extending the distal portion of the cannula 109 past the distal end of the introducer 100 until a needle 130 attached to the distal end of the cannula 109 is placed at a desired radial distance from the axis defined by the sheath of the introducer. The method may further comprise rotating the introducer 100 to position the needle 130 at a desired position. The method may further comprise moving the introducer in a distal direction to insert the needle 130 into the bladder. The method may further include activating the syringe to inject OnabotulinumtoxinA into the bladder. The method may further include moving the introducer 100 in a proximal direction to remove the needle 130 from the bladder. The method may further include repeating the extending, rotating, moving distally, activating, and moving proximally steps until a therapeutically effective amount of OnabotulinumtoxinA has been injected in a therapeutically effective pattern into the bladder.

Figure 7A:
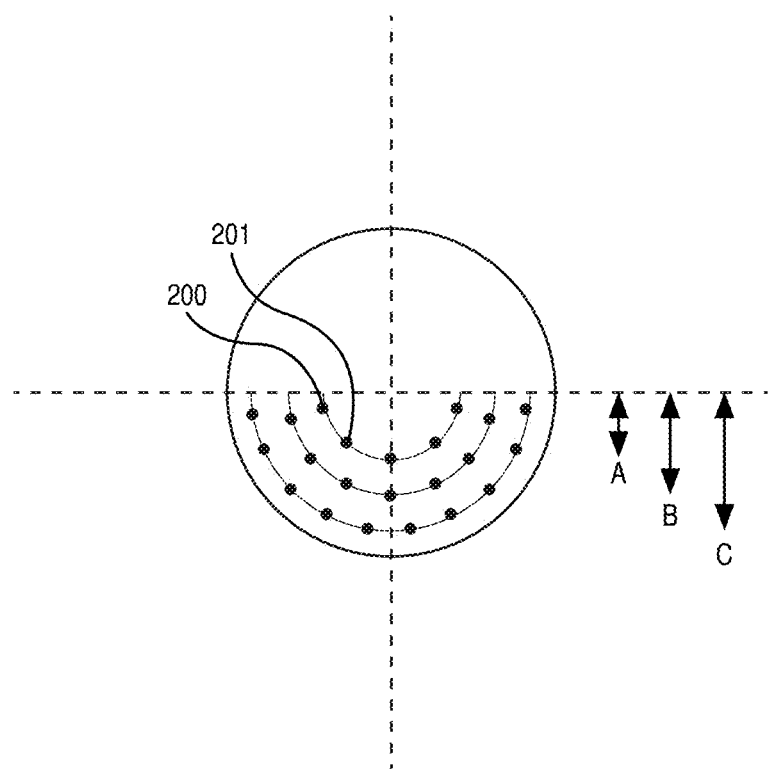
FIG. 7A is a frontal view diagram of a bladder injection pattern according to one embodiment of the present invention.
Figure 7B:
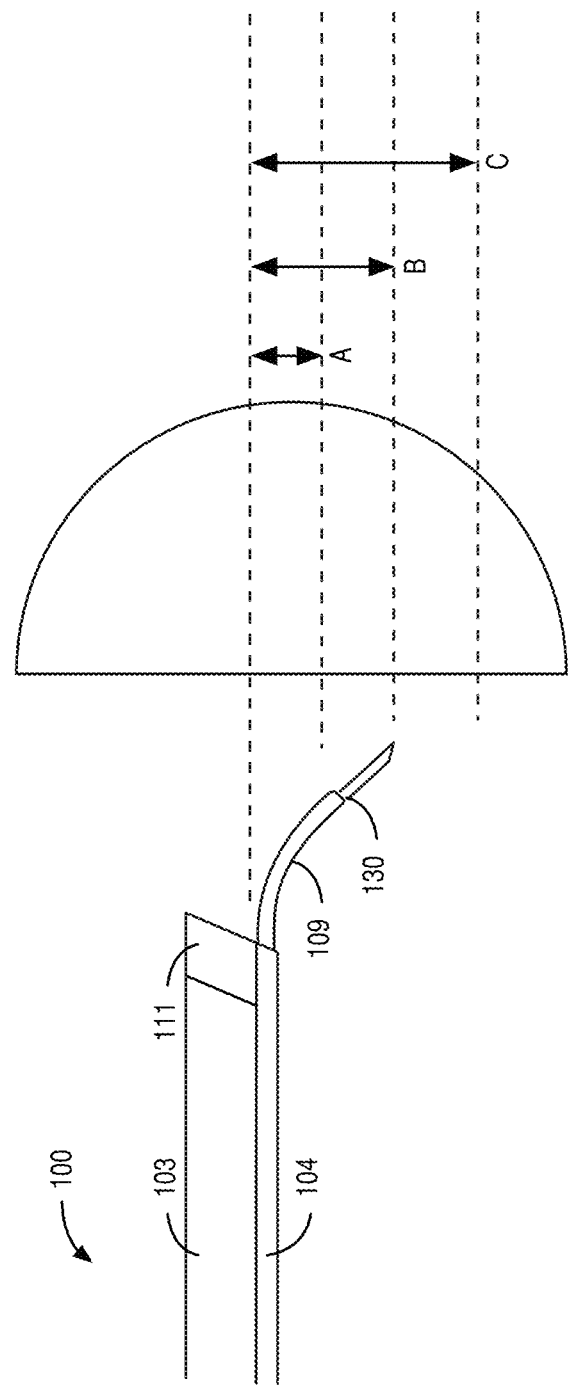
FIG. 7B is a side view diagram of a bladder injection pattern according to one embodiment of the present invention.

Referring now to FIGS. 7A and 7B, therapeutically effective patterns of injections according to at least one embodiment of the present invention is shown. It is beneficial to disperse the injections of OnabotulinumtoxinA across the bladder tissue. In preferred embodiments, injections patterns may comprise three concentric semi-circles in the lower half of the bladder with radii A, B, and C. Such an injection pattern may be created by moving the cannula 109 distally until the needle 130 is at a distance A from the axis defined by the sheath 102 of the introducer 100. The introducer 100 may then be rotated until the needle 130 is at injection site 200. The introducer 100 may be moved distally to inject the bladder with OnabotulinumtoxinA and then moved proximally to withdraw the needle 130 from the bladder. The introducer 100 may then be rotated counterclockwise until the needle 130 is at injection site 201, and the injection process may be repeated. Once the injection pattern for the semi-circle with radius A is complete, the cannula 109 may be moved distally until the needle 130 is at a distance B from the axis defined by the sheath 102 of the introducer 100, and the previous steps may be repeated to create the injection patterns for the semi-circles with radii B and C.

Preferably, A is approximately 0.43 inches, B is approximately 0.8 inches, and C is approximately 1.2 inches.

By rotating the introducer 100 to position the needle rather than moving the introducer 100 laterally, the patient experiences less discomfort and possible injury from lateral stretching of the urethra.

Throughout the process, the cap 111 allows the endoscope 110 to remain isolated from the external environment including the bodily fluids of the patient, maintaining the sterility of the endoscope 110. The introducer 100 and cannula 109 may be disposed after the procedure, obviating the need to sterilize any equipment used during the procedure.

The above description and drawings are illustrative and are not to be construed as limiting the invention to the precise forms disclosed. Persons skilled in the relevant art can appreciate that many modifications and variations are possible in light of the above disclosure. Numerous specific details are described to provide a thorough understanding of the disclosure. However, in certain instances, well-known or conventional details are not described in order to avoid obscuring the description.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or any combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the disclosure provided herein can be applied to other systems, not necessarily the system described above. The elements and acts of the various embodiments described above can be combined to provide further embodiments.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms may be highlighted, for example using capitalization, italics and/or quotation marks. The use of highlighting has no influence on the scope and meaning of a term; the scope and meaning of a term is the same, in the same context, whether or not it is highlighted. It will be appreciated that same element can be described in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example reference to "an additive" can include a plurality of such additives, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments, +/−10%, in some embodiments +/−5%, in some embodiments +/−1%, in some embodiments +/−0.5%, and in some embodiments, +/−0.1%, from the specified amount, as such variations are appropriate in the disclosed products and methods.

The invention claimed is:

1. A medical injection assembly comprising:
   an introducer comprising:
      a handle;
      a sheath extending distally from said handle along a longitudinal axis;
      a scope lumen in said sheath, extending along said longitudinal axis and configured to receive an endoscope at a first proximal portion of the handle and hold the endoscope in a desired position;
      an optically-clear, fluid-tight cap attached to a distal end of the scope lumen and configured to isolate the scope lumen from the external environment;
      said cap having a distal end that conforms to a plane angled at about 60 degrees to said longitudinal axis;
      a cannula lumen in said sheath, extending along said longitudinal axis and configured to receive a cannula at a second proximal portion of the handle and hold the cannula in a desired position;
      at least one fluid lumen in said sheath, extending along said axis and configured to channel fluid to and from a distal end of the sheath;
   a cannula slidingly received in said cannula lumen and configured such that the distance, in a direction transverse to said longitudinal axis, between a distal tip of the cannula and said longitudinal axis increases as the cannula is moved in a distal direction out of the cannula lumen, wherein said distance increases over at least a part of the motion of the cannula tip after emerging from the cannula lumen;
   an injection needle affixed to the distal tip of the cannula;
   a first fluid connector attached to a proximal end of the cannula;
   wherein the cannula is comprised of a biocompatible thermoplastic polymer; and
   wherein a distal portion of the cannula, after said distal portion of the cannula has been pushed distally out of the cannula lumen, reverts to and maintains a predefined curvature shaped as an inverse tangent function in the absence of a deforming force; and
   a syringe connected to the proximal end of the cannula.

2. The medical injection assembly of claim 1, wherein the optically-clear, fluid-tight cap is comprised of silicon.

3. The medical injection assembly of claim 1, wherein the optically-clear, fluid-tight cap is configured to deform to the shape of the endoscope without distorting the optical properties of the endoscope.

4. The medical injection assembly of claim 1, wherein the optically-clear, fluid-tight cap is over molded to the distal end of the scope lumen.

5. The medical injection assembly of claim 1, wherein the diameter of the needle is less than the diameter of the cannula.

6. The medical injection assembly of claim 1, wherein the needle is a 23-gauge needle.

7. The medical injection assembly of claim 1, wherein the biocompatible thermoplastic polymer has a flexural modulus of about 595,000 psi.

8. The medical injection assembly of claim 7, wherein the biocompatible thermoplastic polymer is polyether etherketone (PEEK).

9. The medical injection assembly of claim 1 further comprising: an endoscope.

10. The medical injection assembly of claim 9, wherein the endoscope is a cystoscope.

11. A medical injection assembly comprising:
   an introducer comprising a handle and a sheath extending distally from the handle along a longitudinal axis and having:
      a scope lumen configured to receive an endoscope at a first proximal portion of the handle, said scope lumen extending distally in the sheath, along said longitudinal axis, and further configured to hold the endoscope in a desired position; and
      a cannula lumen configured to slidingly receive a cannula at a second proximal portion of the handle and extending in the sheath, along said longitudinal axis;
   an optically-clear, fluid-tight cap attached at a distal end of the scope lumen and configured to isolate the scope lumen from the external environment;
   wherein said cap has a planar distal end inclined relative to said longitudinal axis at an angle of approximately 60 degrees;
   a cannula configured to slide inside the cannula lumen along said longitudinal axis and having a distal portion terminating in a distal end;
   wherein the entirety of the cannula is a continuous tube of a biocompatible polymer;
   an injection needle affixed to and extending distally from the distal end of the cannula;
   said distal portion of the cannula reverting to a predefined curvature after exiting the cannula distally during said sliding motion and thereby causing said needle to move in a direction transverse to said longitudinal axis as the cannula slides out of the cannula lumen, wherein said distance increases over at least a part of the motion of the cannula tip after emerging from the cannula lumen;
   wherein said predefined shape to which the cannula reverts after exiting the cannula lumen in a distal direction is defined by an inverse tangent function.

12. The medical injection assembly of claim 11, in which said cannula is configured to insert said injection needle into a patient's bladder to inject Botox therein when pushed in the distal direction.

13. The medical injection assembly of claim 11, in which said cannula is make of a PEEK material.

14. The medical injection assembly of claim 13 in which said cannula has a flexural modulus of about 595,000 psi.

* * * * *